United States Patent [19]

Landwehr

[11] Patent Number: 5,442,444
[45] Date of Patent: Aug. 15, 1995

[54] APPARATUS FOR HUMAN TOPOGRAPHY

[76] Inventor: Ulrich M. Landwehr, Vahrenwalder Str 7, 30165 Hannover, Germany

[21] Appl. No.: 207,276

[22] Filed: Mar. 7, 1994

[51] Int. Cl.⁶ .................. G01B 11/24; G03B 15/00; G03B 29/00
[52] U.S. Cl. .................. 356/376; 354/77; 354/62; 354/290; 353/28; 353/40
[58] Field of Search .......... 356/375, 376, 379, 374, 356/2, 1; 354/77, 62, 290, 75, 76, 78; 353/28, 30, 40, 94; 128/774, 779, 782; 348/782, 783

[56] References Cited

U.S. PATENT DOCUMENTS

| | | | |
|---|---|---|---|
| 2,870,672 | 1/1959 | Gage et al. | 353/28 |
| 4,473,750 | 9/1984 | Oshida et al. | 356/376 |
| 4,786,925 | 11/1988 | Landwehr | 356/376 |
| 4,894,551 | 1/1990 | Kishimoto et al. | 356/376 |
| 4,895,448 | 1/1990 | Laird | 356/376 |
| 4,987,432 | 1/1991 | Landwehr | 356/376 |

*Primary Examiner*—Hoa Q. Pham
*Attorney, Agent, or Firm*—Ralf H. Siegemund

[57] ABSTRACT

An apparatus for determining the dimensions of an object such as a person uses a video or diskette or still camera, and includes further two projectors for projecting a horizontal raster line pattern at a 45° angle onto the person, so that projected lines as imaged appear in superimposed relation to the person also as imaged; there is an improvement which includes a horizontal overhead mirror or a pair of horizontally positioned overhead concave mirrors, the projectors being oriented so that the raster as projected is directed towards the mirror(s) at a 45° angle to that mirror, so that the projection beam is reflected at a 45° angle accordingly.

8 Claims, 1 Drawing Sheet

APPARATUS FOR HUMAN TOPOGRAPHY

BACKGROUND OF THE INVENTION

The present invention relates to a device for ascertaining the dimensions of an object in a general sense, and particularly a human being; and more particularly the invention relates to acquiring topological measurements of a person by projecting a pattern of horizontal raster lines onto the body of that object (person), at a 45° projection angle and under utilization of a mirror; an image is produced of the surface of that object upon which is superimposed that projected line pattern.

Devices of the kind to which the invention pertains are known for example from German patent application A1 38 31 630; see also U.S. Pat. No. 4,987,432 issued Jan. 22, 1991. This known device includes a projector for the projection of a raster line pattern, the projector being arranged behind a stand on which the person stands. The mirror is inclined at an angle of about 67.5° relative to the ceiling of the room in which the device or apparatus is used. More particularly, the mirror is fastened to that ceiling and hangs more or less down from there, at a location between the camera and the stand.

While generally satisfactory it was found that this arrangement has a number of drawbacks. The projector for the line raster and the camera for acquiring the topographic, image information, basically face each other, and since the projection may use a flash the imaging process may be interfered with on that account.

More of a problem however is the mirror itself which, simply speaking, is often in the way. Consider the fact that the line pattern must extend for at least 1,200 mm while the mirror will extend down from the ceiling by about a meter. Assuming that normally rooms have a height of 2.5 to 2.8 meters, that (physical) projection or extension of the mirror in a downward direction can be a considerable hindrance. It can easily be seen that in a situation involving haste or something similar, the mirror could easily be hit and damaged or at least misadjusted. Also it was found that the fastening of the mirror is surprisingly complicated.

Further to the state of the art see U.S. Pat. Nos. 4,786,925; 4,639,107 and 4,370,039.

DESCRIPTION OF THE INVENTION

It is an object of the present invention to provide a new and improved device generally as outlined above but eliminating the problems as stated, whereby particularly the installation and adjustment of the mirror and the projector are to be facilitated while misadjustment and pushing the mirror out of its original alignment is essentially avoided.

It is therefore a specific object of the present invention to improve the ascertainment of topographic data of an object such as a person upon whom a line pattern is projected at an angle of 45°, and wherein the object (person) is imaged together with the reflection of that line raster pattern as projected.

The objects of the invention and here particularly the specific object are attained by projecting the line pattern towards and onto a horizontally oriented overhead mirror for reflection in a downward direction towards the object (person), the projection angle is to be at least approximately 45°. Preferably two projectors are used, with the beams intercepting in the plane of projection. The mirror may be divided into two each, being of a concave contour. The two projectors are arranged one behind the other, either in direct horizontal relation or in vertically staggered relation.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a room A in which has been placed the inventive device and apparatus. The room has a ceiling C and a floor F. It has of course also sidewalls but that is not relevant for the invention nor in fact needed. To the left is shown as placed a regular or still video camera or a CCD camera which may be connected to a computer, which is not shown, because the invention concerns only the projection of rasters. Alternatively, the camera may have a diskette or a regular film as the image receiving medium.

Figure 1:
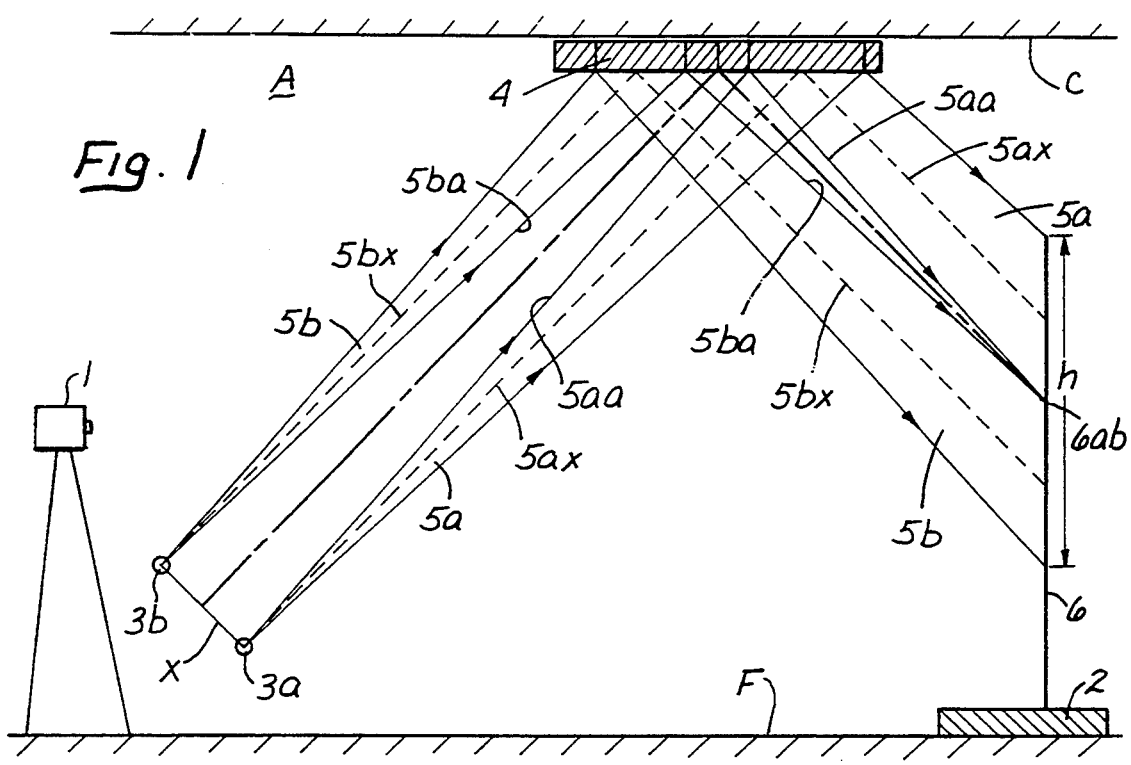
FIG. 1 is a somewhat schematic side view of a preferred embodiment for practicing the best mode of the invention.

The purpose of the camera is to image a person who stands on a balancing stand 2. A stand suitable for this purpose is for example described in U.S. Pat. No. 4,928,708. The surface contour of the person standing on stand 2 is to be ascertained and particularly is to be three-dimensionally measured by way of an imaging procedure for the topographic surface of that person facing the camera or away therefrom. The imaging is described in detail in U.S. Pat. No. 4,370,039 and others mentioned in the introduction.

Two image projectors 3a and 3b are used in order to project a raster line pattern onto the person standing on stand 2. These projectors may use slides for that purpose. If 1 is a video camera then the projectors may operate on a continuous basis or stroboscopically. In the case of a diskette or regular photographic camera the projectors 3a and 3b are flash projectors projecting the respective line patterns simultaneously while the camera 1 acquires an image.

The projectors are shown schematically only, whereby it is an essential feature that they are spaced by a distance or spacing or axis X, being situated in a vertical plane, the line—spacing—distance—axis X having a 45° angle relative to the horizontal and the vertical. In other words, the two projectors are spaced horizontally and staggered vertically (or vice versa). Aside therefrom the projectors may have a common housing or connected housings that stands on the floor F of the room A and are (is) preferably firmly connected thereto.

The projectors project beams 5a and 5b respectively towards an overhead mirror 4 which is flat; that is, it extends horizontally while being secured to the ceiling C accordingly. The reflected beams and beam rays all meet (i.e. are intercepted by the vertical plane 6 of projection which is not a real object), but that aspect is described also in principle in the above mentioned U.S. Pat. No. 4,370,039. The person to be topographically measured must stand in that plane or at least very near thereto.

Each projector has an optical projection system such as an objective lens or lens system having a focal length of at least 100 mm. The focal length is optimal when the projection image of the line pattern in plane 6 extends for a height of 1.2 meter. The respective outer lines 5aa and 5ba of the respective line pattern image producing beams 5a,b intersect preferably in the plane in the point 6ab. The two rays 5aa and 5ab have between them an angle of not more than 6°.

The axis rays of the two beams, 5ax and 5bx are oriented and placed to intercept at least approximately the seat area and the back of the person standing on stand 2, in or near the plane 6 and facing away from the camera. The optical axes of the projectors that is the axes along which the central beams 5ax and 5bx are projected have exactly an angle of 45° in relation to the flatly arranged mirror 4. The degree of deflection of an imaged line that "hits" the mirror is equal to the height of a curving (the tangents of 45° is equal to 1) out of the plane 6. Thus the orientation of the projector beams is designed so that particularly in the central back as well as in the seat area of a person bulging contours are represented by significant deflections of image lines from the horizontal.

Figure 2:
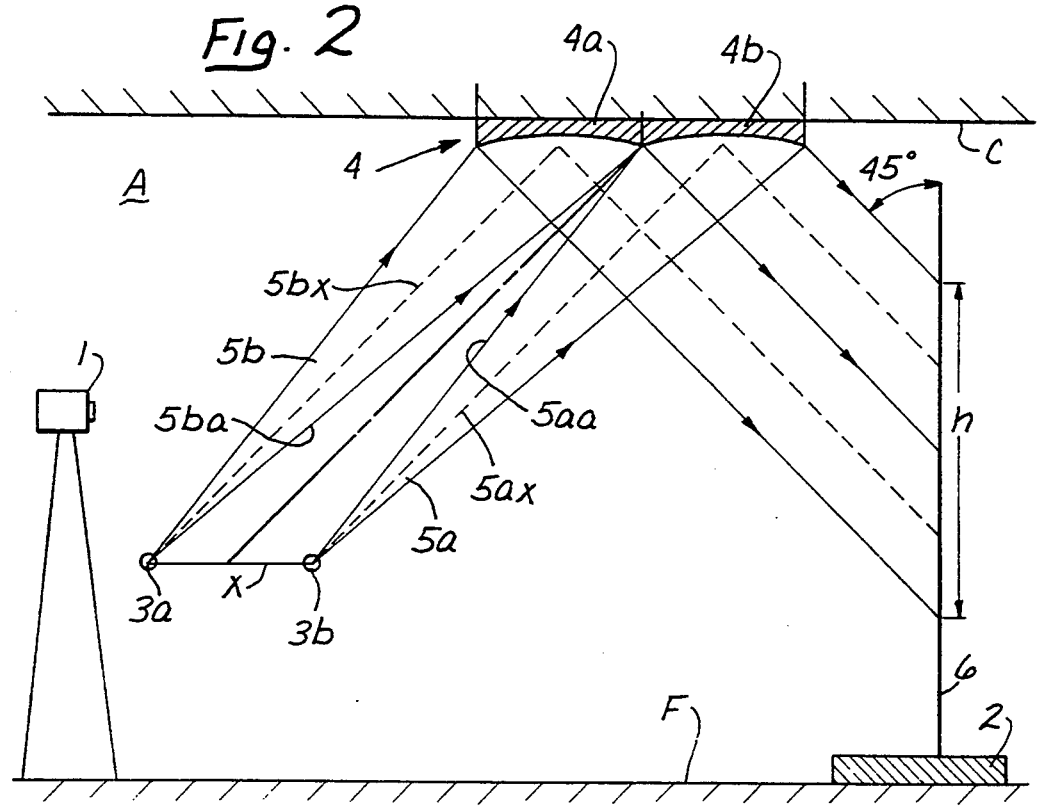
FIG. 2 is a modification but still being a preferred embodiment and a best mode configuration.

The embodiment shown in FIG. 2 shows basically the same equipment as described thus far. However the two projectors 3a and 3b are here spaced by the line—axis X which extends in the horizontal only, and accordingly, there is no vertical staggering of the projectors. The optical axes and beams 5ax and 5bx are also here oriented at 45° to the plane of mirror 4. Thus there is also a projection of the raster lines along this 45° orientation. A sharp projection of the lines over the entire projection depth for fully open objective aperture (large diaphragm opening) results through the depth of field and is attained in that the slides having the raster to be imaged are obliquely positioned on the optical axis of projection as per the so-called Scheimpflug method.

The mirror 4 is actually segmented in this embodiment, there being segments or two mirrors 4a and 4b accordingly. Each of the segments constitutes a mirror on its own, and concave contours have been chosen for them. The concave surfaces are coated as reflecting. The two concave mirrors 4a,b are configured and arranged so that the lines as they are reflected by them will all be reflected at exactly a 45° angle and at the same distance as between any adjacent two lines (the raster lines of the slides being projected are of course equidistantly spaced). In other words the concave mirrors have a collimating effect on the respective beams which leave them mirrors 4a,b as parallel bundles. The two rays 5aa and 5ab intersect in the mirror plane.

As a consequence of the foregoing, the focal lengths of the projecting, objective lenses (or lens systems) are smaller in this embodiment than in the one of FIG. 1 (all other parameters, particularly of the room are the same; moreover the same slide (i.e. one can be a direct copy of the other one) can be chosen here for the two projectors. The line rasters are chosen so that each relatively thick line is succeeded in the raster pattern by two thinner ones etc. The distance of the projected lines to each other in plane 6 of projection is about 10 mm. This is deemed best for a visual evaluation of human body contours.

The invention is not limited to the embodiments described above but all changes and modifications thereof, not constituting departures from the spirit and scope of the invention, are intended to be included.

I claim:

1. Apparatus for acquiring dimensions of an object by means of imaging, and including projection means for projecting a horizontal raster line pattern at a 45° angle onto that object, so that lines of the projected line pattern are imaged in superimposed relation to that object, the improvement comprising;
   said projection means including two projectors, each for projecting a raster into a common plane for both of the projectors;
   a horizontal overhead mirror, said projection means being oriented so that the raster line pattern is projected upwardly by means of a projection beam being directed towards the mirror at a 45° angle from below toward that mirror, so that the projection beam is reflected at a 45° angle and downwardly accordingly.

2. Apparatus as in claim 1, said projection means being provided for focussing at a focal length of at least 100 mm.

3. Apparatus as in claim 1, said mirror having two concave mirror surfaces.

4. Apparatus as in claim 1, the raster including lines of different thicknesses.

5. Apparatus as in claim 1, said imaging means being a video camera, or a diskette camera, or a still camera.

6. Apparatus for acquiring dimensions of an object by means of imaging, and including projection means for projecting a horizontal raster line pattern at a 45° angle onto that object, so that lines of the projected line pattern are imaged in superimposed relation to that object, the improvement comprising;
   a horizontal overhead mirror being comprised of two concave mirrors, said projection means being oriented so that the raster line pattern is projected upwardly by means of a projection beam being directed towards the mirror at a 45° angle from below toward that mirror, so that the projection beam is reflected at a 45° angle and downwardly accordingly that is toward an object and from above.

7. Apparatus as in claim 4, said projection means including two projectors, each for projecting a raster into a common plane for both of the projectors.

8. Apparatus as in claim 7, said two projectors each having a projection beam, the two beams intersecting in the projection plane.

* * * * *